(12) United States Patent
Arreola

(10) Patent No.: US 8,312,055 B2
(45) Date of Patent: Nov. 13, 2012

(54) CONTENT ALERT UPON AVAILABILITY FOR INTERNET-ENABLED TV

(75) Inventor: Orlando Arreola, San Diego, CA (US)

(73) Assignee: Sony Corporation, Tokyo (JP)

( * ) Notice: Subject to any disclaimer, the term of this patent is extended or adjusted under 35 U.S.C. 154(b) by 256 days.

(21) Appl. No.: 12/813,919

(22) Filed: Jun. 11, 2010

(65) Prior Publication Data

US 2011/0307508 A1 Dec. 15, 2011

(51) Int. Cl.
*G06F 17/30* (2006.01)
(52) U.S. Cl. ........ 707/802; 707/803; 707/805; 707/613; 707/758; 707/769; 340/539.1; 340/546; 709/206; 715/753; 715/758; 455/567; 345/710
(58) Field of Classification Search .......... 707/802–803, 707/805, 613; 709/206; 340/539.1, 546; 715/753, 758; 455/567; 345/710
See application file for complete search history.

(56) References Cited

U.S. PATENT DOCUMENTS

| | | | |
|---|---|---|---|
| 5,444,433 A * | 8/1995 | Gropper | 340/601 |
| 5,635,980 A * | 6/1997 | Lin et al. | 725/131 |
| 5,986,650 A | 11/1999 | Ellis et al. | |
| 8,144,006 B2 * | 3/2012 | Thomas | 340/539.1 |
| 2004/0061716 A1 * | 4/2004 | Cheung et al. | 345/710 |
| 2004/0082345 A1 * | 4/2004 | Lueckhoff | 455/456.3 |
| 2004/0162879 A1 * | 8/2004 | Arcuri et al. | 709/206 |
| 2004/0266491 A1 * | 12/2004 | Howard et al. | 455/567 |
| 2005/0028106 A1 * | 2/2005 | Nelson et al. | 715/753 |
| 2006/0161853 A1 * | 7/2006 | Chen et al. | 715/758 |
| 2008/0059995 A1 * | 3/2008 | Shanks et al. | 725/32 |
| 2008/0077673 A1 * | 3/2008 | Thomas | 709/206 |
| 2008/0127271 A1 | 5/2008 | Zriny et al. | |
| 2009/0043786 A1 | 2/2009 | Schmidt et al. | |
| 2009/0063649 A1 | 3/2009 | Yamagishi | |
| 2009/0150925 A1 | 6/2009 | Henderson | |
| 2010/0009651 A1 * | 1/2010 | Daly et al. | 455/404.1 |
| 2010/0176943 A1 * | 7/2010 | Snell | 340/540 |
| 2011/0153754 A1 * | 6/2011 | Gunasekara | 709/206 |
| 2011/0197223 A1 * | 8/2011 | Ravula | 725/33 |

* cited by examiner

*Primary Examiner* — Frantz Coby
(74) *Attorney, Agent, or Firm* — John L. Rogitz

(57) ABSTRACT

The user of an Internet-enabled CE device such as an Internet protocol TV (IPTV) can enter search terms describing desired Internet-sourced programs, and Internet channels are monitored to detect when the desired programs become available. When a desired program is detected an alert appears on screen, which can be selected to navigate to a current alert user interface (UI) from which detected desired programs can be selected for presentation.

20 Claims, 4 Drawing Sheets

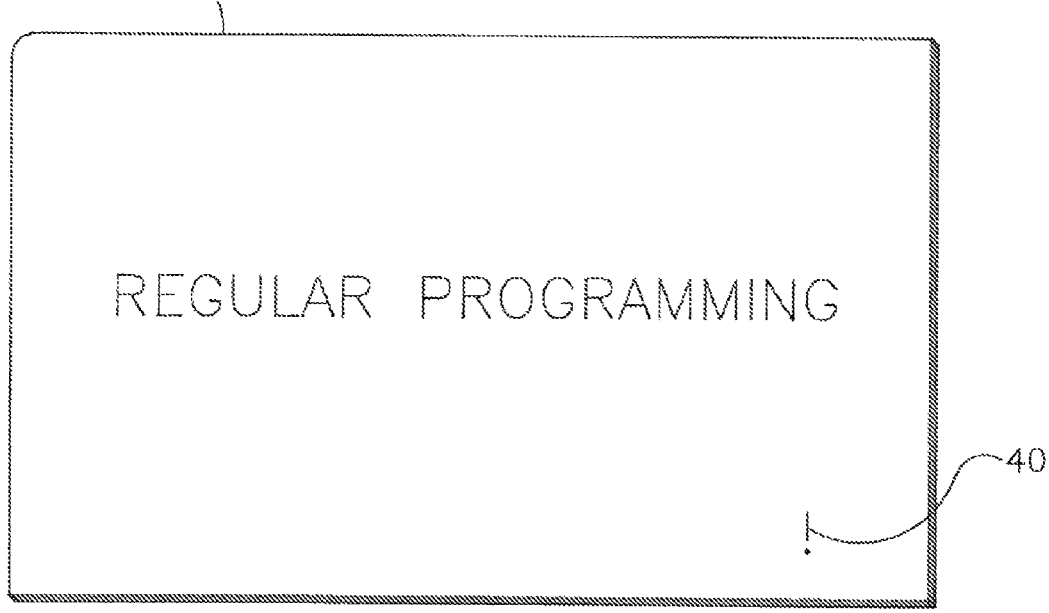
FIG. 4 ALERT SCREEN
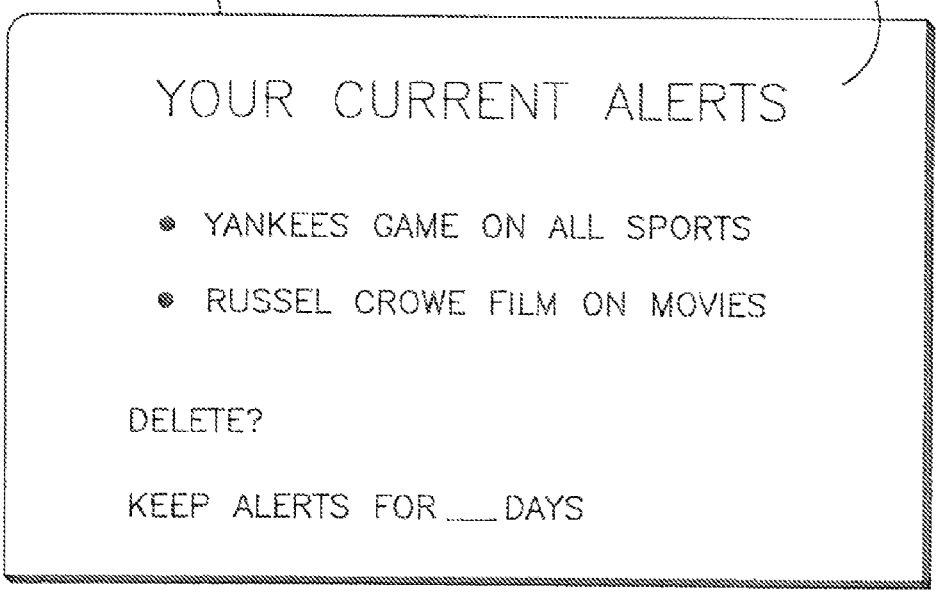
FIG. 5 ALERT BROWSE USER INTERFACE

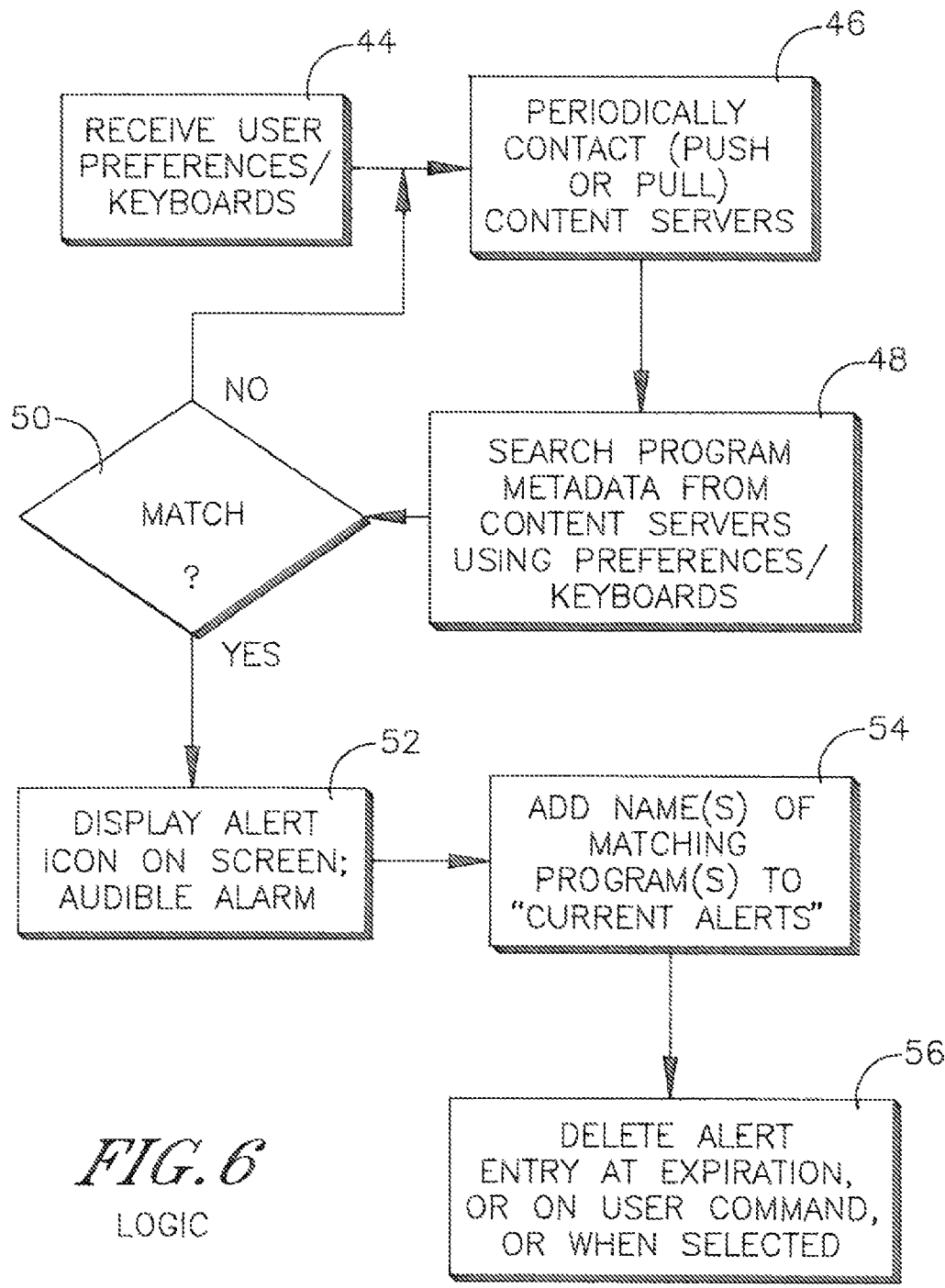
FIG. 6 LOGIC

CONTENT ALERT UPON AVAILABILITY FOR INTERNET-ENABLED TV

FIELD OF THE INVENTION

The present application relates generally to alerting users of Internet-enabled TVs when desired Internet content becomes available.

BACKGROUND OF THE INVENTION

Internet access through TVs is typically provided by essentially programming the TV as though it were a computer executing a browser. Such Internet access is thus uncontrolled except as a firewall or filtering program might block certain sites.

As understood herein, uncontrolled Internet access may not be desirable in the context of a TV. A firewall or filtering program may not always be installed on the TV and even when one is installed, access remains much more uncontrolled than conventional TV programming traditionally has expected. Also, a locally installed filter can be unloaded or defeated by a user.

Accordingly, uncontrolled Internet access has several drawbacks. From a viewer's standpoint, exposure to inappropriate subject matter particularly when young viewers are watching is one concern; a much lower threshold of quality screening is another. That is, while many TV shows might not be widely considered as "quality" shows, nonetheless a TV program is usually much more selectively screened than, say, an Internet video. The expectations of TV viewers for such higher level quality screening as a consequence cannot be met by simply providing unfettered Internet access through the TV. Furthermore, TV-related entities, from content providers, manufacturers, and carriers, in most cases derive no benefit from the extension of TV to the Internet.

As further recognized herein, even in a structured and controlled Internet Protocol TV (IPTV) system the Internet content will change constantly and can also grow. Unlike televised content, however, IPTV systems may not provide electronic program guides (EPGs) for Internet content or may not update such guides quickly enough to account for rapidly changing Internet programming. Thus, a user can more easily miss a desired Internet-sourced program.

Furthermore, a desired Internet-sourced program may be difficult to find in the first place, requiring Internet-type searching on the part of the user. Searching, however, is effective only for locating current content, not future content.

SUMMARY OF THE INVENTION

Accordingly, a CE device includes a housing, a display on the housing, a network interface, and a processor in the housing controlling the display and communicating with the Internet through the network interface. The processor executes logic that includes receiving user preferences and/or keywords via a user interface (UI) presented on the display and periodically communicating with one or more content servers via the network interface to retrieve program metadata of audio video content. Further, the logic includes searching the program metadata received from the content servers using the preferences/keywords. Responsive to a determination that a match exists between the metadata of an Internet-sourced piece of content and the preferences/keywords, the logic presents on the display a visual alert and/or presenting on the speaker an audible alert indicative of a match to indicate to a user that new content conforming to the preferences and/or keywords is available for play on the CE device.

In some embodiments the logic further includes, responsive to a determination that a match exists between the metadata of an Internet-sourced piece of content and the preferences/keywords, adding a name of a program found to match on a "current alert" list and presenting the current alert list upon invocation thereof on the display.

If desired, an entry on the current list may be deleted at the elapse of the user-defined expiration period, upon user command to delete, and/or when the entry is selected from list for play.

The CE device can initiate communication with the content servers to access the metadata. Or, the CE device can wait until a content server that has updated the content available communicates new metadata to the CE device. The preferences/keywords can be uploaded to the content server which performs search and match logic and return an indication thereof to the CE device.

In another aspect, an apparatus includes a housing, a display on the housing, a speaker, a network interface, and a processor in the housing controlling the display and speaker and communicating with the Internet through the network interface. The processor executes logic that includes presenting on the display a user preferences and/or keywords entry user interface (UI) and responsive to a determination that content satisfying the user preferences and/or keywords which was not available at the time of entering the user preferences and/or keywords has become available at an Internet server, presenting on the display an alert icon to indicate the availability of content. Responsive to an invocation of a current alert UI, a UI listing a name of the content in a current list is presented on the display. The current alert UI is usable to select the content for presentation on the display.

In another aspect, a method includes receiving from a user of an Internet-enabled CE device search terms describing desired Internet-sourced programs. The method also includes monitoring at least one Internet source to detect when the desired programs become available, and responsive to a determination that a desired program is detected, generating a signal representative thereof useful for presenting an alert on a screen of the device.

The details of the present invention, both as to its structure and operation, can best be understood in reference to the accompanying drawings, in which like reference numerals refer to like parts, and in which:

BRIEF DESCRIPTION OF THE DRAWINGS

FIG. 4 is a screen shot of an example content alert;

FIG. 5 is a screen shot of an example Current Alert UI; and

FIG. 6 is a flow chart of example logic in accordance with present principles.

DETAILED DESCRIPTION OF THE PREFERRED EMBODIMENT

Figure 1:
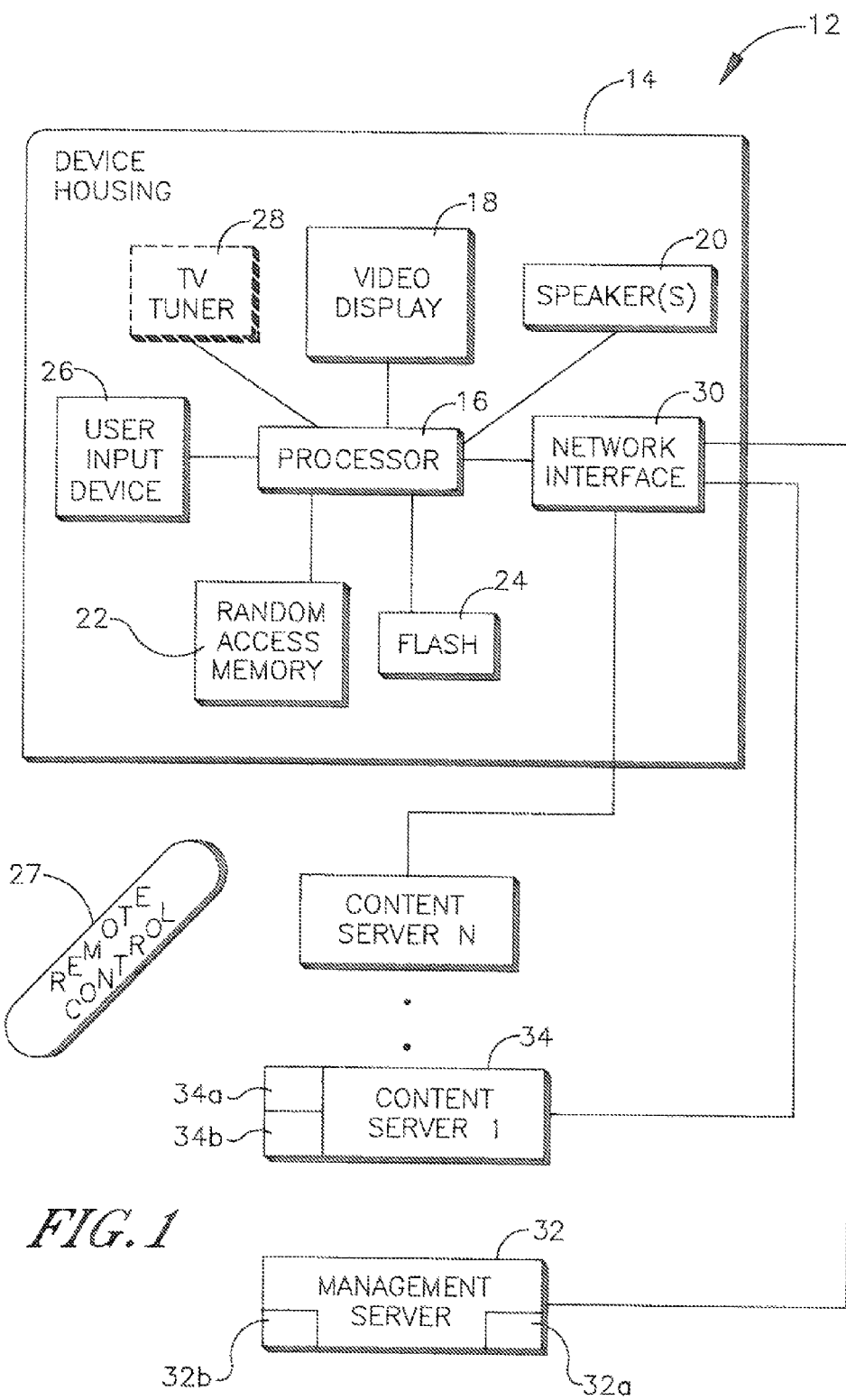
FIG. 1 is a block diagram of an example system in accordance with present principles.

Referring initially to FIG. 1, a consumer electronics (CE) device 12 such as a TV, game player, video disk player, camera, digital clock radio, mobile telephone, personal digital assistant, laptop computer, etc. includes a portable lightweight plastic housing 14 bearing a digital processor 16. The processor 16 can control a visual display 18 and an audible display 20 such as one or more speakers.

To undertake present principles, the processor 16 may access one or more computer readable storage media such as but not limited to RAM-based storage 22 (e.g., a chip implementing dynamic random access memory (DRAM)) or flash memory 24. Software code implementing present logic executable by the CE device 12 may be stored on one of the memories shown to undertake present principles.

The processor 16 can receive user input signals from various input devices, including a keypad 26, a remote control device 27, a point and click device such as a mouse, a keypad, etc. A TV tuner 28 may be provided in some implementations particularly when the CE device is embodied by a TV to receive TV signals from a source such as a set-top box, satellite receiver, cable head end, terrestrial TV signal antenna, etc. Signals from the tuner 28 are sent to the processor 16 for presentation on the display 18 and speakers 20.

As shown in FIG. 1, a network interface 30 such as a wired or wireless modem or wireless telephony transceiver communicates with the processor 16 to provide connectivity to a management server 32 on the Internet and to one or more content servers 34. The servers 32, 34 have respective processors 32*a*, 34*a* and respective computer readable storage media 32*b*, 34*b*. It is to be understood in view of disclosure below that the CE device 12 particularly when implemented by a non-PC device such as a TV or game console or camera can communicate only with the management server 32 and with content servers 34 that appear on a service list provided to the processor 16 by the management server 32, with the service list not being modifiable by the processor 16. In any case, the content servers 34 are participants in the IPTV system to gain entry onto the service list.

Figure 2:
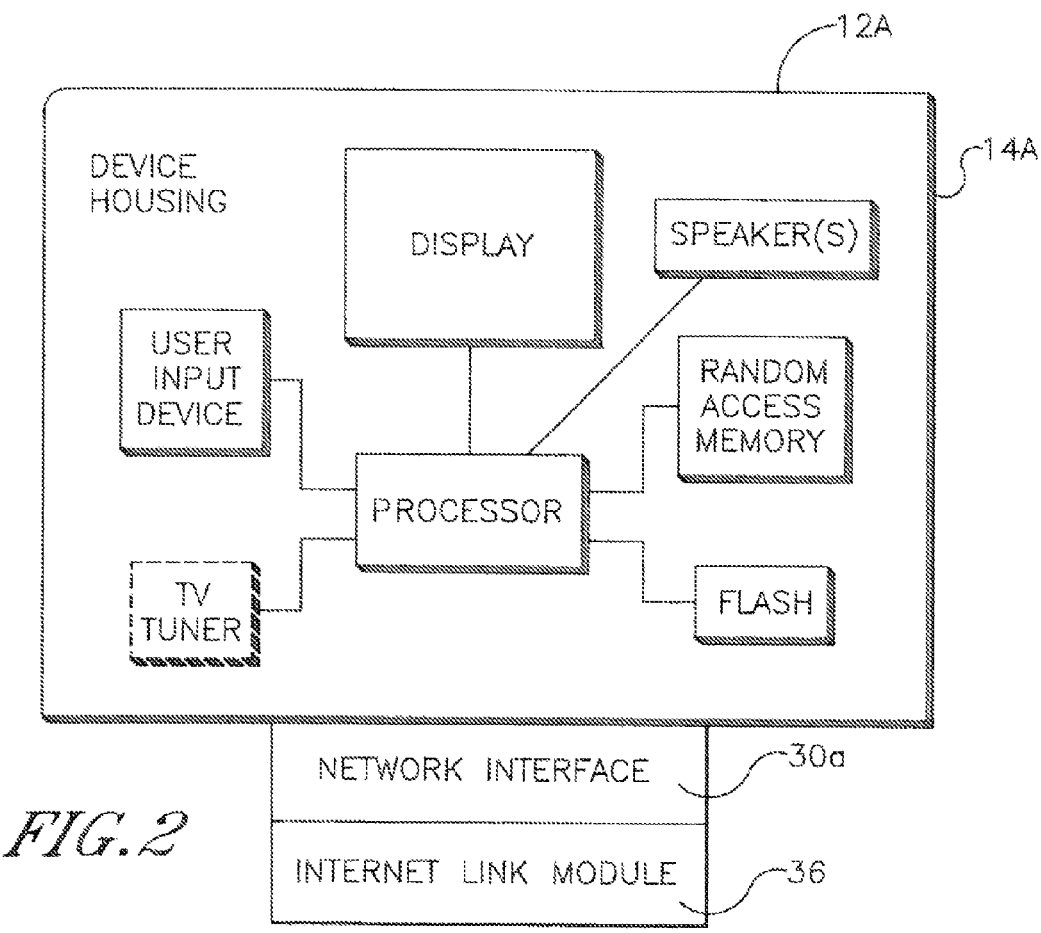
FIG. 2 is a block diagram of another example system in accordance with present principles.

FIG. 2 shows a CE device 12*a* that in all essential respects is identical to the device 12 shown in FIG. 1, except that a network interface 30*a* is not located within the device housing 14*a* but instead is supported in a separate Internet link module housing 36 that may be mounted on the device housing 14*a*.

Figure 3:
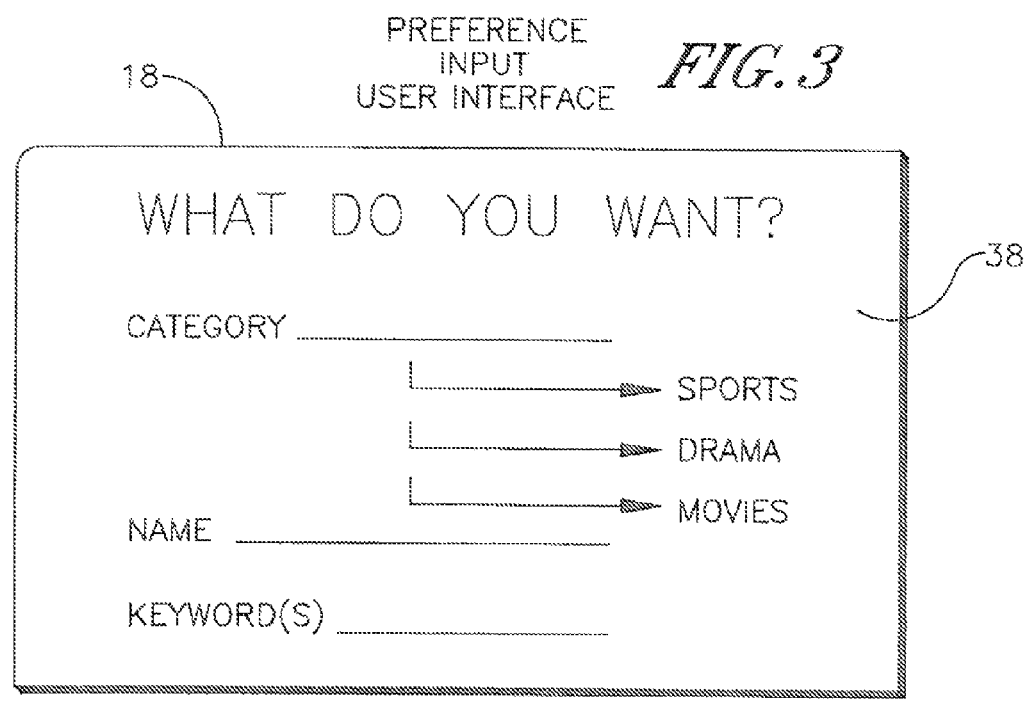
FIG. 3 is a screen shot of an example user interface (UI) for inputting Internet Protocol TV (IPTV) viewing preferences from the Internet.

Now referring to FIGS. 3-5, various screen shots that can be presented on the display 18 in example embodiments are shown. A preference entry user interface (UI) 38 is shown in FIG. 3 may include, as shown, a category entry field. A user may manipulate one of the above-described input devices to enter the text of a desired category, e.g., "sports", and/or a user can simply click on the category field to cause a drop-down menu of categories to be displayed as shown, from which menu a category may be selected.

Additionally, a program name field may be provided as shown, into which a user may enter the name of a particular program, e.g., "Yankees Game". Further, a keyword field may be provided into which a user may enter keywords such as "victory" or "Jeter homerun" to further narrow subsequent searching for a desired program. The user preference entries are saved in one of the above-disclosed memory devices.

Based on the preferences, search logic is executed and example logic is described further below. Upon detection of a desired program from an Internet source, FIG. 4 shows that a visual alert icon 40 is presented in the display 18. An audible alert such as a beep or other audible alarm may also be presented on the speakers 20 to indicate the detection of a desired program on the Internet. In the non-limiting example shown, the alert icon 40 is an exclamation mark, although other visual alerts, including text descriptions of detected desired programs displayed near, e.g., the bottom of the screen may be used.

FIG. 5 shows that responsive to a user clicking on or hovering over the icon 40, a current alert UI 42 may be presented on the display 18. The current alert UT 42 may also be navigated to from another TV menu. In any case, the current alert UI 42 lists desired programs which were searched for and found on one of the content servers 34 responsive to preference search terms input using the UI 38 of FIG. 3.

If desired, the UI 42 in FIG. 5 may also present an option, selectable by the user, to delete an entry by, e.g., highlighting the entry using one of the user input devices described above and pressing "Y" or some other designated key to indicate that the highlighted alert or alerts should be deleted. The UI 42 may also include an expiration field into which a number of days (or hours, or weeks, etc.) may be entered by the user for maintaining a detected program in the current alert UI 42, after which period a detected program is removed from the list. Still further, a program may be automatically removed from the list once selected (as by clicking on it) for presentation on the CE device 12.

Now referring to FIG. 6, at block 44 the user preferences and/or keywords are received via, e.g., the UI 38 of FIG. 3. Block 46 indicates that the CE device 12 periodically communicates with one or more of the content servers 34 to retrieve metadata of program content. In some embodiments, the CE device 12 may initiate the communication ("pull"). In other embodiments, the CE device 12 may wait until a content server 34 that has updated the content available through the IPTV system in which the content server 34 is participating communicates new metadata to the CE device 12 ("push").

Proceeding to block 48, the CE device 12 searches the program metadata received from the content servers using the preferences/keywords received at block 44. It is to be understood that alternatively, the preferences/keywords can be provided to the content servers 34, which perform the search and match logic and return an indication thereof to the CE device 12.

Decision diamond 50 indicates that as a result of the search at block 48, the CE device 12 determines whether a match exists between the metadata of an Internet-sourced piece of content and the preferences/keywords received at block 44. If a match exists, at block 52 an alert such as the icon 40 in FIG. 4 is presented on the display 18, and if desired or alternatively an audible alert is played on the speakers 20. Also in the event of a match, the names of any matching programs found at states 48 and 50 are added at block 54 to the "current alert" list shown in FIG. 5. Should the user select the icon 40, the UI 42 of FIG. 5 may be presented to give the user a fuller understanding of what desired program has been discovered and is ready for play. Block 56 simply indicates that alert entries may be deleted at the elapse of the user-defined expiration period, and/or upon user command to delete, and/or when the entry is selected from list in FIG. 5 for play.

Alternative to clicking on the "alert" icon 40 to select content, a predeterminedley on, e.g., the RC 27 (such as "enter" or "return") may be toggled to select newly available Internet-sourced content for play. If desired, an autofill feature may be provided such that during the input of preferences, the CE device 12 makes suggestions of potential preferences or automatically fills the preference field based on the first few letters input by the user. After a predetermined period of time from its appearance, the icon 40 preferably is removed from view on the display 18. Also, the CE device 12 may provide for individual user login, in which case the search results based on a particular user's preferences/keywords are kept separate from those pertaining to other users. The UI 42 of FIG. 5 in this embodiment presents only program matches for the particular user who last logged in and is assumed to be the current user.

While the particular CONTENT ALERT UPON AVAILABILITY FOR INTERNET-ENABLED TV is herein shown and described in detail, it is to be understood that the subject matter which is encompassed by the present invention is limited only by the claims.

What is claimed is:

1. Consumer electronics (CE) device comprising:
   housing;
   display on the housing;
   audio speaker;
   network interface;
   processor controlling the display and speaker and communicating with the Internet through the network interface;
   the processor executing logic including:
   receiving user preferences and/or keywords via a user interface (UI) presented on the display;
   periodically communicating with one or more content servers via the network interface to retrieve program metadata of audio video content;
   searching the program metadata received from the content servers using the preferences/keywords;
   responsive to a determination that a match exists between the metadata of an Internet-sourced piece of content and the preferences/keywords, presenting on the display a visual alert and/or presenting on the speaker an audible alert indicative of a match to indicate to a user that new content conforming to the preferences and/or keywords is available for play on the CE device.

2. The CE device of claim 1, wherein the logic further includes, responsive to a determination that a match exists between the metadata of an Internet-sourced piece of content and the preferences/keywords, adding a name of a program found to match on a "current alert" list and presenting the current alert list upon invocation thereof on the display.

3. The CE device of claim 1, wherein the logic further comprises deleting an entry on the current list at the elapse of a user-defined expiration period.

4. The CE device of claim 1, wherein the logic further comprises deleting an entry on the current list upon user command to delete.

5. The CE device of claim 1, wherein the logic further comprises deleting an entry on the current list when the entry is selected from list for play.

6. The CE device of claim 1, wherein the logic further comprises initiating communication with the content servers to access the metadata.

7. The CE device of claim 1, wherein the logic further comprises waiting until a content server that has updated the content available communicates new metadata to the CE device.

8. The CE device of claim 1, wherein the logic further comprises providing preferences/keywords to the content server which performs search and match logic and return an indication thereof to the CE device.

9. Apparatus comprising:
   housing;
   display on the housing;
   audio speaker;
   network interface;
   processor controlling the display and speaker and communicating with the Internet through the network interface;
   the processor executing logic including:
   presenting on the display a user preferences and/or keywords entry user interface (UI);
   responsive to a determination that content satisfying the user preferences and/or keywords which was not available at the time of entering the user preferences and/or keywords has become available at an Internet server, presenting on the display an alert icon to indicate the availability of content; and
   responsive to an invocation of a current alert UI, presenting on the display a UI listing a name of the content in a current list, the current alert UI being usable to select the content for presentation on the display.

10. The apparatus of claim 9, wherein the logic further includes:
    periodically communicating with one or more content servers via the network interface to retrieve program metadata of audio video content;
    searching the program metadata received from the content servers using the preferences/keywords; and
    responsive to a determination that a match exists between the metadata of an Internet-sourced piece of content and the preferences/keywords, presenting on the display the visual alert and presenting on the speaker an audible alert indicative of a match to indicate to a user that new content conforming to the preferences and/or keywords is available for play on the apparatus.

11. Apparatus of claim 10, wherein the logic further comprises deleting an entry on the current list at the elapse of a user-defined expiration period.

12. Apparatus of claim 10, wherein the logic further comprises deleting an entry on the current list upon user command to delete.

13. Apparatus of claim 10, wherein the logic further comprises deleting an entry on the current list when the entry is selected from list for play.

14. Apparatus of claim 10, wherein the logic further comprises initiating communication with the content servers to access the metadata.

15. Apparatus of claim 10, wherein the logic further comprises waiting until a content server that has updated the content available communicates new metadata to the apparatus.

16. Method comprising:
    receiving from a user of an Internet-enabled consumer electronics (CE) device search terms describing desired Internet-sourced programs;
    monitoring at least one Internet source to detect when the desired programs become available; and
    responsive to a determination that a desired program is detected, generating a signal representative thereof useful for presenting an alert on a screen of the device.

17. The method of claim 16, wherein the method is executed by an Internet server.

18. The method of claim 16, wherein the method is executed by the CE device and the method further includes:
    responsive to selection of the alert, presenting on the screen a current alert user interface (UI); and
    responsive to selection of an entry on the current alert UI, playing content underlying the entry on the device.

19. The method of claim 18, further comprising:
    periodically communicating with one or more content servers via a network interface to retrieve program metadata of audio video content; and
    searching the program metadata received from the content servers using user-entered preferences and/or keywords describing the desired Internet-sourced programs.

20. The method of claim 17, deleting an entry at the elapse of a user-defined expiration period and/or when the entry is selected for play.

* * * * *